United States Patent [19]

Van der Knaap

[11] Patent Number: Plant 6,103

[45] Date of Patent: Feb. 9, 1988

[54] CHRYSANTHEMUM PLANT NAMED CASSA

[75] Inventor: Jacques C. M. Van der Knaap, De Lier, Netherlands

[73] Assignee: Fides, Handelskwekerij, De Lier, Netherlands

[21] Appl. No.: 820,795

[22] Filed: Jan. 22, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Cassa particularly characterized by its flat capitulum form and single daisy capitulum type; clear white ray floret color; diameter across the face of the capitulum of 40–60 mm; and yellow-green to yellow disc florets.

1 Drawing Figure

The present invention comprises a new and distinct cultivar of Chrysanthemum, botanically known as *Dendranthema morifolium*, Ramat., previously *Chrysanthemum morifolium*, Ramat., and referred to by the cultivar name Cassa.

Cassa is a product of a planned breeding program which had the objective of creating new Chrysanthemum cultivars with single daisy capitulum type, clear white ray floret color, 9 week response, low temperature tolerance and the ability to produce commercially acceptable quality in year around cut mum programs. Such traits in combination were not present or needed improvement in previously available commercial cultivars.

Cassa was originated from a hybridization made in a controlled breeding program in De Lier, The Netherlands in 1979. The female parent was White Marguerite, an unpatented cultivar. The male parent of Cassa was Smile, also unpatented. Cassa was discovered and selected as one flowering plant within the progeny of the stated cross by Jacques C. M. Van der Knaap in May of 1979, in a controlled environment in De Lier, The Netherlands.

The first act of asexual reproduction of Cassa was accomplished when vegetative cuttings were taken from the initial selection in June of 1979 in a controlled environment in De Lier, The Netherlands by a technician working under formulations established and supervised by Jacques C. M. Van der Knaap. Horticultural examination of selected units initiated in November of 1979 has demonstrated that the combination of characteristics as herein disclosed for Cassa are firmly fixed and are retained through successive generations of asexual reproduction.

Cassa has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Cassa which, in combination, distinguish this Chrysanthemum as a new and distinct cultivar:

1. Flat capitulum form.
2. Single daisy capitulum type.

3. Clear white ray floret.
4. Diameter across the face of the capitulum 40–60 mm.
5. Yellow-green (immature) to yellow (mature) disc florets.

Of the many commercial cultivars known to the present inventor, the most similar in comparison to Cassa is White Marguerite, the female parent. In comparison to White Marguerite, Cassa has different foliar and floral characteristics. The disc floret color, capitulum form and capitulum type of Cassa are similar to those same characteristics of White Marguerite.

The accompanying photographic drawing shows typical inflorescence and foliage characteristics of Cassa. The photograph is in black and white, with two flowers being colored to accurately depict ray and disc floret colors.

In the following description, color references are made to The Royal Horticultural Society Colour Chart. The color values were determined between 11:00 a.m. and 12:00 noon in April of 1981 under natural day light at De Lier, The Netherlands.

Classification:

*Botanical.*—*Dendranthema morifolium*, Ramat., cv Cassa.

*Commercial.*—Cut daisy spray.

INFLORESCENCE

A. Capitulum:

*Form.*—Flat.

*Type.*—Daisy.

*Diameter across face.*—40–60 mm.

B. Corolla of ray florets:

*Color (general tonality from a distance of three meters).*—White.

*Color (upper surface).*—R.H.S. 155D.

*Color (under surface).*—R.H.S. 155D.

C. Corolla of disc florets:

*Color (mature).*—Yellow.

*Color (immature).*—Yellow-green.

D. Reproductive organs:

*Androecium.*—Present in disc florets, numerous.

*Gynoecium.*—Present in both disc and ray florets; numerous.

PLANT

A. General appearance:

(Continued on next page.)

*Height.*—80 cm.

B. Foliage:

*Color* (*upper surface*).—R.H.S. 147B.

*Color* (*under surface*).—R.H.S. 147A.

*Shape.*—Short lobed and finely serrated.

I claim:

1. A new and distinct Chrysanthemum plant named

Cassa, as described and illustrated, and particularly characterized by its flat capitulum form and single daisy capitulum type; clear white ray floret color; diameter across the face of the capitulum of 40–60 mm; and yellow-green to yellow disc florets.

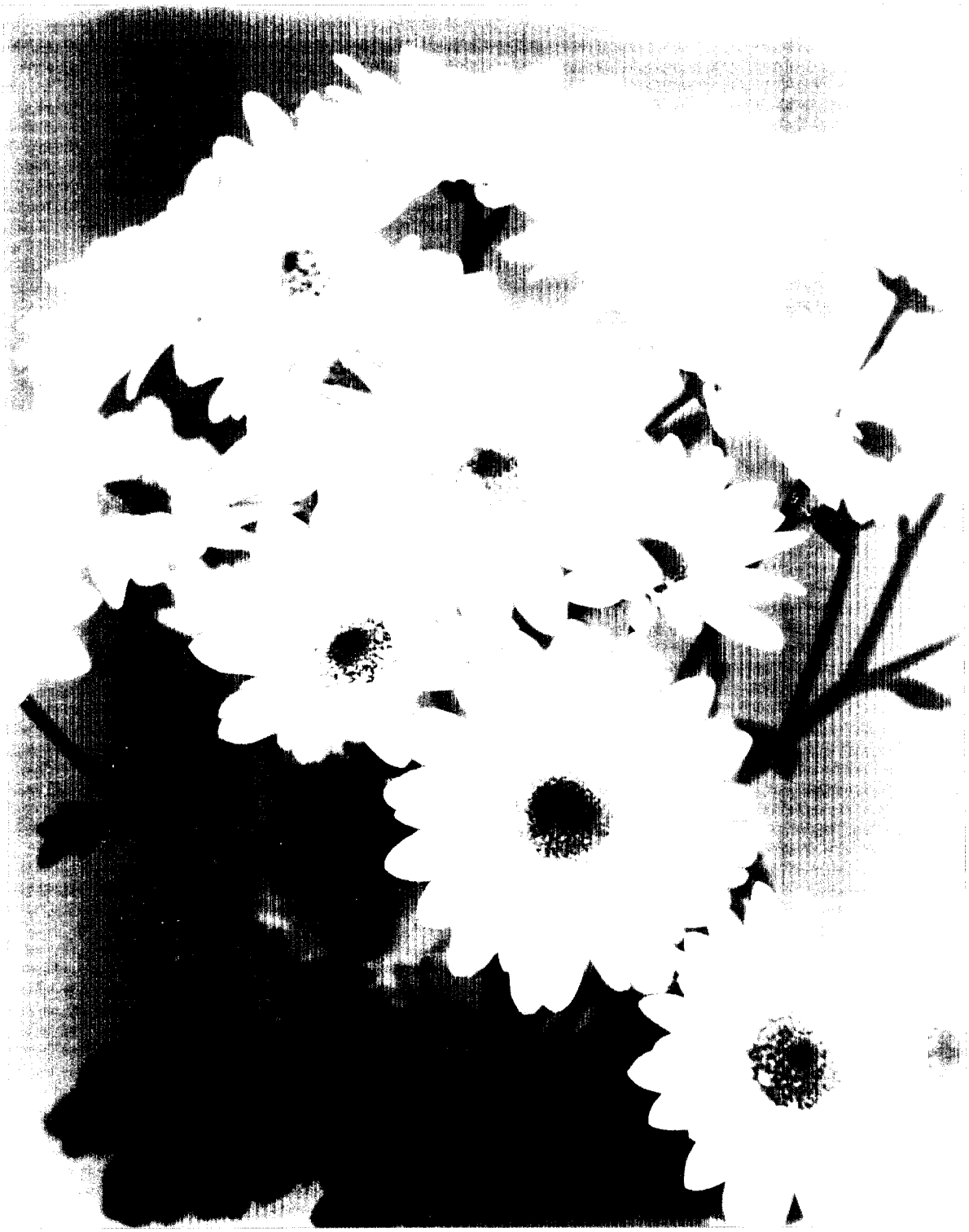

* * * * *